US012688910B2

(12) United States Patent　(10) Patent No.:　US 12,688,910 B2
Yu et al.　(45) Date of Patent:　Jul. 21, 2026

(54) SYSTEM AND METHOD FOR CONFIGURATION, SCHEDULING, AND/OR EXECUTION OF ANALYZING SERVICES FOR MEDICAL DATA BASED ON USAGE DATA

(71) Applicant: SIEMENS HEALTHINEERS AG, Forchheim (DE)

(72) Inventors: Daphne Yu, Yardley, PA (US); Anthony Dass Sowrirajan, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 596 days.

(21) Appl. No.: 17/447,606

(22) Filed: Sep. 14, 2021

(65) Prior Publication Data

US 2022/0101963 A1　Mar. 31, 2022

(30) Foreign Application Priority Data

Sep. 30, 2020 　(DE) ..................... 10 2020 212 411.6

(51) Int. Cl.
　*G16H 10/60*　(2018.01)
　*G06N 3/08*　(2023.01)
　*G06Q 10/0633*　(2023.01)
(52) U.S. Cl.
　CPC .............. *G16H 10/60* (2018.01); *G06N 3/08* (2013.01); *G06Q 10/0633* (2013.01)
(58) Field of Classification Search
　CPC ....... G16H 10/60; G06Q 10/0633; G06N 3/08
　USPC .......................................................... 705/3
　See application file for complete search history.

(56) References Cited

U.S. PATENT DOCUMENTS

| 11,763,944 | B2 | 9/2023 | Chen et al. |
| 2008/0175460 | A1* | 7/2008 | Reiner .................... G06F 16/26 |
| | | | 707/E17.019 |
| 2009/0138318 | A1 | 5/2009 | Hawkins et al. |
| 2010/0161345 | A1 | 6/2010 | Cain et al. |
| 2015/0331995 | A1 | 11/2015 | Zhao et al. |

(Continued)

FOREIGN PATENT DOCUMENTS

| CN | 111542897 | A | 8/2020 |
| CN | 111916202 | A | 11/2020 |

(Continued)

OTHER PUBLICATIONS

Melnik, M., & Nasonov, D. (2019). Workflow scheduling using neural networks and reinforcement learning. Procedia computer science, 156, 29-36. (Year: 2019).*

(Continued)

*Primary Examiner* — Winston R Furtado

(57)　ABSTRACT

A medical data processing system includes: a medical data storage configured to collect one or more pieces of medical data from one or more input devices, a data analyzer configured to execute one or more analyzing services on the one or more pieces of medical data so as to output one or more corresponding pieces of analyzed medical data, a results manager configured to collect usage data, related to how the one or more pieces of analyzed medical data are analyzed by the data analyzer and/or used by one or more users, and a processing optimizer configured to control operation of the data analyzer based on the usage data.

11 Claims, 3 Drawing Sheets

(56) References Cited

U.S. PATENT DOCUMENTS

| | | | |
|---|---|---|---|
| 2016/0147954 A1* | 5/2016 | Ng Tari | ................. G16H 40/20 |
| | | | 705/3 |
| 2017/0169173 A1 | 6/2017 | Snow, Jr. et al. | |
| 2019/0206561 A1 | 7/2019 | Shelton, IV et al. | |
| 2019/0325304 A1* | 10/2019 | Gottin | .................... G06N 3/045 |
| 2020/0111578 A1* | 4/2020 | Koblick | ................. G16H 80/00 |
| 2020/0357515 A1* | 11/2020 | Chen | ........................ G06N 7/01 |
| 2022/0101963 A1 | 3/2022 | Yu et al. | |

FOREIGN PATENT DOCUMENTS

| | | |
|---|---|---|
| CN | 114334103 A | 4/2022 |
| KR | 20160122460 A | 10/2016 |
| WO | 2018013666 A1 | 1/2018 |

OTHER PUBLICATIONS

Vasilyeva, Ekaterina, Mykola Pechenizkiy, and Seppo Puuronen. "Towards the framework of adaptive user interfaces for eHealth." 18th IEEE Symposium on Computer-Based Medical Systems (CBMS'05). IEEE, 2005.

German Office mailed Jun. 23, 2021 in corresponding German Patent Application No. 10 2020 212 411.6.

\* cited by examiner

SYSTEM AND METHOD FOR CONFIGURATION, SCHEDULING, AND/OR EXECUTION OF ANALYZING SERVICES FOR MEDICAL DATA BASED ON USAGE DATA

RELATED APPLICATION

This application claims the benefit of DE 10 2020 212 411.6, filed Sep. 30, 2020, which is hereby incorporated by reference in its entirety.

BACKGROUND

Modern medical equipment is often capable of producing output in the form of digital data. Examples thereof can be, for instance, images from a magnetic resonance scanner or from an X-ray scanner, electrocardiogram and blood pressure data, temperature of a patient, etc. With the increase in digitalization, the number of medical devices capable of outputting data in digital form is ever increasing.

The outputted pieces of medical data, for instance an X-ray image, a resonance scanner image, etc. can be subjected to one or more analyzing services. Generally, those analyzing services are configured to extract salient information from the medical data and/or present the medical data and the salient information in a more effective manner to a user, for instance a radiologist or a doctor. An example of such service can be an AI-based analysis configured to recognize specific pattern in the X-ray image, a rule-based scoring of the content of the image, or an identification of regions of the image in need of further review by a radiologist, etc.

Those analyzing services are generally software-based and thus require a certain amount of computational resources to be executed. As computational resources are generally limited, the lack of computational resources can become a bottleneck in various manners. In general, during any given period, a limited number of analyzing services can be executed on a number of pieces of medical data.

This can lead to various issues, depending on how the execution of the analyzing services is controlled.

For instance, the order of the analyzing services can be problematic. As an example, a case in which less urgent analyzing service, such as a scoring of a mass suspected of being a tumor, is executed prior to a more urgent analyzing service, such as an AI-based analysis of a X-ray image of a heart believed to suffer from an heart attack. This might happen for instance because the former was requested prior to the latter, in a first-in-first-out approach, while the opposite situation would be preferable.

Alternatively, or in addition, it is possible that different users of the results of the analyzing services might have different preferences in which analyzing services they find more useful. For instance, a given radiologist might find the result of analyzing service 1 to provide better insights than analyzing service 2, while this might be the opposite for another radiologist. Executing only analyzing service 1 on all incoming pieces of medical data is useless for the second radiologist, which will likely require analyzing service 2 to be executed on the pieces of medical data directed to him, thus resulting in delayed and less efficient work from the radiologist. Similarly, executing both analyzing services 1 and 2 on all incoming pieces of medical will make an inefficient use of the computational resources.

Moreover, different radiologists might have different processing orders in how the analyzed medical data are perused.

For instance, a first radiologist might prefer to start from more complex analysis while another radiologist might prefer to start from simpler analysis. Providing the pieces of analyzed medical data to the radiologists in the order they have been analyzed, with a first-in-first-out approach, might thus not comply with the approach of each radiologist, thus making their work less efficient.

There is therefore a need to control the execution of analyzing services so that efficiency can be increased in how the execution of those services makes use of available computational resources and how the resulting pieces of analyzed medical data are shown to the various users.

SUMMARY

In general, data related to how the output of the various analyzing services is used by the users can be used as feedback in order to optimize the application of the analyzing services to the pieces of medical data as well as to the configuration of the workflows illustrating the output of the analyzing services to the users. Such user feedback can be generally provided as input to a medical data processing system or method, preferably based on a reinforcement learning approach. Still preferably, the user feedback can be provided during time, allowing a continuous training of the medical data processing system or method.

An aspect can therefore relate to a medical data processing system including: a medical data storage configured to collect one or more pieces of medical data from one or more input devices, a data analyzer configured to execute one or more analyzing services on the one or more pieces of medical data so as to output one or more corresponding pieces of analyzed medical data, a results manager configured to collect usage data, related to how the one or more pieces of analyzed medical data are analyzed by the data analyzer and/or used by one or more users, and a processing optimizer configured to control operation of the data analyzer based on the usage data.

In this manner, it is advantageously possible to use a statistic derived from the usage data concerning how the users, such as medical personnel, for instance radiologists, make use of the results provided by the data analyzer. In this manner, it is possible to know, for instance, which services provided by the data analyzer are the most used, when they are used, the computational resources needed, and plan the operation of the data analyzer accordingly.

The usage data can be seen as analytics related to when/how the results of the data analyzer are perused, possibly as a function of the specific medical data type and/or the specific user. By using those analytics as an input to an optimizing algorithm, it is possible to render the operation of the data analyzer optimized in view of one or more constraints and one or more objectives.

According to some aspects, the processing optimizer can be configured to control operation of the data analyzer by controlling: which of the one or more analyzing services is executed on which of the one or more pieces of medical data, a level of computing resources made available for the execution of the one or more analyzing services on the one or more pieces of medical data, and/or a scheduling for executing the one or more analyzing services on the one or more pieces of medical data.

That is, the configuration, scheduling, and/or execution of the various analyzing services can be controlled based on how the users make use of the results they provide. This has the advantage of adapting the data analyzer to best serve the users. Moreover, as the adaptation can be performed at various time points, it is also possible to adapt to variation of preferences by the users and/or to variations introduced by new users operating in the hospital.

According to some aspects, the usage data can include one or more of a queueing time, based on a time from collecting of the one or more pieces of medical data to executing of the one or more analyzing services on the one or more pieces of medical data, an analyzing time, based on a time used for executing of the one or more analyzing services on the one or more pieces of medical data, correlation between use of the one or more pieces of analyzed medical data by the one or more users, and meta-data associated to the one or more pieces of medical data.

Thanks to this approach it is generally possible to configure the data analyzer to reduce the queuing time and/or the analyzing time as well as improving the use of relevant data analyzing services as a function of the medical data to be analyzed. This last point can be achieved by distinguishing which kind of medical data, such as related to which kind of medical field and/or condition is being analyzed. This can be done by automatically recognizing the medical data inputted and/or by using meta-data of the medical data, such as text strings providing a more or less specific description of the medical data associated to the meta-data.

According to some aspects, the medical data processing system can further include a configuration storage configured to store configuration data, related to processing preferences, wherein the processing optimizer can further be configured to control operation of the data analyzer based on the configuration data.

The presence of the configuration storage allows hospital specific policies to be described, for instance by defining constraints, objectives through natural language expressions, and/or by assigning weights to predetermined constraints and/or objectives. In this manner the operation of the processing optimizer can be influenced in view of specific hospital and/or department policies.

According to some aspects, the medical data processing system can further include a workflow analytics engine configured to evaluate the usage data so as to identify, for a given user of the one or more users, how the one or more pieces of analyzed medical data are used by the given user, wherein the results manager can further be configured to output the one or more pieces of analyzed medical data to a plurality of output devices based on the results of the evaluation of the workflow analytics engine.

In addition to the advantages described in relation to the processing optimize, the workflow analytics engine allows the results of the data analyzer to be optimized for a user-specific workflow. The user-specific operation of the workflow analytics engine can be based on the usage data previously referred to as well as to user-specific data indicating how the specific user peruse the output of the data analyzer, such as whether output data is used or not whether configurations are kept or modified, whether results are annotated, modified this indicating a higher level of interest in the specific output data, etc.

A further aspect can relate to a method for processing medical data including the acts of: collecting one or more first pieces of medical data from one or more input devices, executing one or more analyzing services on the one or more pieces of medical data, outputting one or more corresponding pieces of analyzed medical data, collecting usage data related to how the one or more analyzing services are executed at the executing act and/or how the one or more pieces of analyzed medical data are used by one or more users, and controlling the executing act for one or more second pieces of medical data, subsequent to the one or more first pieces of medical data, based on the usage data.

According to some aspects, the act of controlling can include controlling which of the one or more analyzing services is executed on which of the one or more first pieces of medical data during the executing act, a level of computing resources made available for execution of the one or more analyzing services on the one or more first pieces of medical data during the executing act, and/or a scheduling for executing the one or more analyzing services on the one or more first pieces of medical data (MD) during the executing act.

According to some aspects, the usage data can includes one or more of a queueing time, based on a time from collecting of the one or more first pieces of medical data to executing of the one or more analyzing services on the one or more first pieces of medical data, an analyzing time, based on a time used for executing of the one or more analyzing services on the one or more first pieces of medical data, correlation between use of the one or more pieces of analyzed medical data by the one or more users, and meta-data associated to the one or more first pieces of medical data.

According to some aspects, the medical data processing method can further include an act of storing configuration data, related to processing preferences, wherein the act of controlling can further be configured to control the executing act for the one or more second pieces of medical data, based on the configuration data.

According to some aspects, the medical data processing method can further include an act of evaluating the usage data so as to identify, for a given user of the one or more users, how the one or more pieces of analyzed medical data are used by the given user, wherein the outputting act can further be configured to output the one or more pieces of analyzed medical data to a plurality of output devices based on the results of the evaluating act.

According to further aspects, a computer program or a computer-program product or a computer-readable storage medium includes program code. The program code can be loaded and executed by at least one processor. Upon loading and executing the program code, the at least one processor can perform any of the method described throughout the application.

It is to be understood that the features mentioned above and those yet to be explained below may be used not only in the respective combinations indicated, but also in other combinations or in isolation without departing from the scope of the invention.

DETAILED DESCRIPTION

Figure 1:
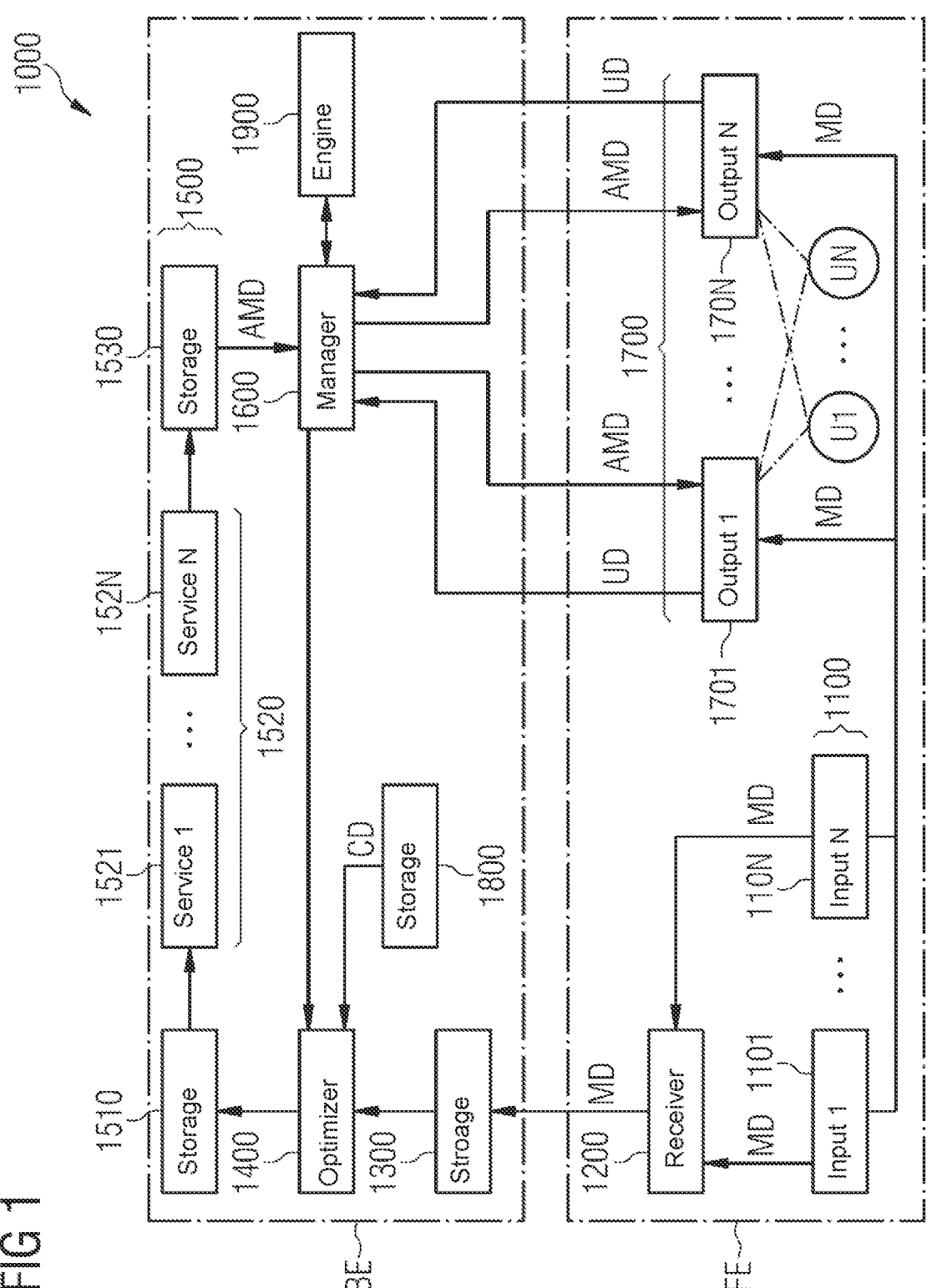
FIG. 1 schematically illustrates a medical processing management system 1000, according to one embodiment.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

According to the techniques described herein, it is possible to manage medical data in a clinical workflow. In particular, it is possible to organize processing and/or analyzing of the medical data in an efficient manner that takes into account hospital policies and preferences of the medical personnel perusing the results of the processing and/or analyzing.

FIG. 1 schematically illustrates a medical data processing system 1000 for processing medical data.

In the context of this application, reference will be made to "medical data." The medical data can generally include any digital data outputted by a measuring instrument designed to measure data, which is medically relevant. Medical data can thus relate to imaging data such as X-rays and magnetic resonance scans, to electrocardiograms, measures of weight, temperature, blood pressure, etc.

In the context of this application, reference will be made to "pieces" of medical data. A piece of medical data can be understood to be medical data outputted in a given session by a given instrument. For instance, a piece of medical data might be one X-ray image, or several X-ray images related to the same patient taken in a single session. In general, this terminology indicates that the medical data that are processed are a plurality and might relate to different patients and/or different diagnosis, so that the medical data are not treated as a continuous flow of data but rather as "packets" or "pieces" of data.

In the context of this application, reference will be made to "analyzing services," executed on the medical data. The analyzing services are generally intended to be various software-based tools for assisting medical personnel, such as doctors or radiologist, in perusing the medical data. Examples of the operation carried out by the analyzing services can include providing findings alert status, computing score values, computing metrics, demarcating regions in need of more detailed analysis, AI-based enhancement, and/or analysis of the medical data, etc.

In the context of this application, reference will be made to "analyzed medical data." The analyzed medical data is generally the result of the operation of the analyzing services on the medical data, possibly provided together with the medical data itself.

An embodiment will now be described with reference to FIG. 1.

As can be seen in FIG. 1, the medical data processing system 1000 can include a medical data storage 1300, configured to collect one or more pieces of medical data MD from one or more input devices 1101-110N.

The input devices 1101-110N can be, in general, any device capable of inputting medically relevant medical data MD such as medical imagining, for instance X-ray machines, nuclear resonance scanners, etc., measuring devices, for instance devices for measuring weight, blood pressure, heart rate, etc., laboratory equipment, as well as PC and/or databases containing medically relevant data, for instance age, weight, sex, medical history, etc., and other devices commonly used in the management of medical data such as PACs (Picture Archive and Communication System), CIS (Clinical Information System), HIS (Hospital Information System), RIS (Radiology Information System), etc. In general, the input devices are capable of outputting such medical data MD in a digital form. In some cases, the medical data MD can further include metadata, such as tags, scores, comments from doctors, keywords etc.

The medical data storage 1300, which can be for instance implemented by a PC, or a server, or more generally by software, stores the various pieces of medical data MD outputted by the input devices 1100.

As it will be clear from the following description, the medical data MD outputted by the input devices 1100 can also be forwarded to one or more output devices 1700 which allow visualization of those medical data. More details on this will be described further below in the description.

In some embodiments, the medical data processing system 1000 can further include a medical data receiver 1200, as illustrated, which generally collects the various pieces of medical data MD from the input devices 1100 and forwards them to the medical data storage 1300. It will be clear that, alternatively or in addition, the medical data MD from the input devices 1100 can also be forwarded directly to the medical data storage 1300, so that the medical data processing system can also be implemented without the medical data receiver 1200.

One advantage of the medical data receiver 1200 is that it can handle the complexity of data collection from a plurality of input devices 1100, many of which operate with different standards, with various kinds of outputs, and then act as a single contact point for the medical data storage 1300. In this manner, the medical data processing system 1000 can be broadly organized with a backend BE and a frontend FE architecture, in which the medical data storage 1300 is part of the backend BE, which can be configured to interoperate with a single, known, medical data receiver 1200, instead of a plurality of different, possibly unknown and potentially changing in time, input devices 1100.

The medical data processing system 1000 can further include a data analyzer 1500, configured to execute one or more analyzing services 1521-152N on the one or more pieces of medical data MD so as to output one or more corresponding pieces of analyzed medical data AMD.

The analyzing services 1521-152N can be executed in series, and/or in parallel, on one or more pieces of medical data MD at any given time. For instance, a first piece of medical data MD1 can be the subject of a first analyzing service 1521 and subsequently of a second analyzing service 1252, while a second piece of medical data MD2 can be the subject of a third analyzing service 1523 and in parallel of a fourth analyzing service 1524.

The analyzing services 1520 are in general software-implemented analysis carried out on the medical data to facilitate interpretation of the medical data by a user U1-UN, for instance a doctor or a radiologist. A variety of such analyzing services are known in the market and any of them could be implemented with the invention.

Workflows for processing of medical data MD by users U1-UN generally differ amongst different hospital institutions. Each institution may specialize more or less at particular disease specialties, may have different number and types of scanners, or more generally different input devices, etc. Moreover, each institution may have different users U1-UN of the medical data MD, such as radiologists, with different work shifts, etc. Moreover, each analyzing service may provide a modality, anatomical and/or disease specific service such as detecting salient anatomical features and derive scores intended to assist the diagnosis during reading. The different analyzing services may be at different levels of maturity in terms of use in routine clinical practices. A hospital may decide to require use of certain analyzing services for some disease as part of his protocol, while some services may be optional or exploratory, etc. It thus follows that each institution is likely to develop specific workflows, based on the use of different analyzing services 1520 depending on a plurality of factors which cannot be known a priori, and which does not have a single best approach but is highly dependent on the characteristics of the medical data MD, and on the working approach of the users U1-UN as well as on hospital policies.

In the illustrated medical data processing system 1000, the data analyzer 1500 further includes a queueing storage 1510 and an analyzed data storage 1530. The queueing storage 1510 generally serves the purpose of storing the pieces of medical data to be analyzed by the data analyzer 1500. The analyzed data storage 1530 generally serves the purpose of storing the results of the analysis carried out by the data analyzer 1500, namely the analyzed medical data AMD. This implementation advantageously allows the data analyzer 1500 to be implemented as a single independent unit. It will however be clear that the invention is not limited thereto, as the function of the queueing storage 1510 and/or of the analyzed data storage 1530 could be implemented by the processing optimizer 1400 and by the results manager 1600, as will become clearer from the following description.

The execution of the one or more analyzing services 1520 on the one or more pieces of medical data MD results in one or more corresponding pieces of analyzed medical data AMD. In general, the pieces of analyzed medical data include additional information compared to the original medical data MD, such as highlighted zones of an image, improved contrast images, scores, etc. In general, the content of the analyzed medical data AMD will depend on the specific analyzing services 1520, it can however be generally said that the analyzed medical data AMD will include additional information compared to the respective medical data MD, resulting from the operation of the analyzing services.

In some embodiments, the analyzed medical data AMD includes only this additional information, while the medical data MD is retrieved by the users U1-UN directly from the input devices 1100. In those cases, a link can be saved between the analyzed medical data AMD and the respective medical data MD so as to allow their identification by the users U1-UN and/or by the output device 1700. This implementation is advantageous in that it lowers the amount of data necessary for storing the analyzed medical data AMD. Alternatively, or in addition, the analyzed medical data AMD could include the original medical data MD in addition to the additional information resulting from the execution of the analyzing services 1520.

In general, the analyzed medical data AMD are accessed by the users U1-UN and perused, preferably together with the respective medical data MD so as to facilitate a diagnosis. The users can do so by one or more output devices 1700. As illustrated, any user U1-UN can in principle access the data from any output device 1700. It will be understood that while the various users can operate any of the output devices, each user might be assigned an account, so as to allow the recognition and/or analyses of data specific to the given user even when the user works on different output devices.

How and/or when the users U1-UN peruse the analyzed medical data AMD, for instance in which order, with which options and/or configuration—where available—for how long, and in general any characteristics related to how the pieces analyzed medical data AMD are perused by the user U1-UN can be collected, in form of usage data UD.

As an example, for a given piece of medical data MD, such an X-ray image, hospital policy might implement two analyzing services 1521 and 1522, providing different types of analysis. It could be that users U1-UN all tend to use the output of analyzing service 1521 and never the output of analyzing service 1522. In this case, the execution of analyzing service 1522 is most likely wasting computational resources of the data analyzer 1500 and/or processing time, at the expenses of the ability of a faster processing of other pieces of medical data MD waiting to be processed. Collecting this information allows reduction of the execution of the analyzing service 1522 on similar types of medical data, without lowering the quality of work of the users U1-UN.

As an additional example, it could also be that a first user U1 regularly uses the output of analyzing service 1521 and never the output of analyzing service 1522 while a second user U2 regularly uses the output of analyzing service 1522 and never the output of analyzing service 1521. In this case, an efficient use of the data analyzer 1500 can be made if it is known whether U1 or U2 will be associated to the given piece of medical data, which can be known for instance based on their current schedule and/or can be decided by the medical data processing system 1000.

As a further example, it could be that execution of an analyzing service 1521 is deemed to take much longer than execution of an analyzing service 1522. In this case, if the output of the analyzing service 1521 is less urgent than the output of the analyzing service 1522, for instance because it relates to a less urgent medical condition, it might be preferable to prioritize execution of the analyzing service 1521 over execution of the analyzing service 1522.

In order to make efficient use of the data analyzer 1500, the embodiment therefore generally makes use of the usage data UD in controlling the operation of the data analyzer

1500. As will be clear from the following, this involves at least an initial training period, in which the usage data UD are collected. Based on those initial data the operation of the data analyzer 1500 can be made to be more efficient in view of the use of the output of the of the data analyzer, represented by the usage data UD.

Moreover, in some embodiments, a continuous training based on the usage data UD can allow the operation of the data analyzer 1500 to adapt to potentially varying usage of the pieces of analyzed medical data AMD. Such varying usage could be caused, for instance, by the analyzing services changing, either in their nature or configuration, and/or by the users U1-UN, and/or their preferences, changing, and/or by the hospital policies and/or medical protocols changing, etc. A continuous training based on the usage data UD thus allows a continuous learning by the system or method of the invention, which can advantageously therefore adapt to the varying situations indicated above.

In particular, the medical data processing system 1000 can further include a results manager 1600 configured to collect the usage data UD, related to how the one or more pieces of analyzed medical data AMD are analyzed by the data analyzer 1500 and/or used by one or more users U1-UN.

In the embodiment of FIG. 1, results manager 1600 is also configured to forward the analyzed medical data AMD to the various output devices 1700. It will be clear that, while this is convenient in that the same unit manages both communications with the output devices 1700, the embodiment is not limited thereto and the two different functions could be implemented by two different units. Alternatively, or in addition, the output units could retrieve the analyzed medical data directly from the data analyzer 1500.

In general, the analyzing services 1520 may be configured to provide viewing of results in a service specific workflow, to examine, annotate, comment, or confirm the results. Any of these input from the users U1-UN, as well as any other access attributes such as time of access of the results, a user ID and profiles, as well as attributes from the medical data MD etc., can be collected as usage data UD and then subsequently used to learn a reader specific optimization, so as to refine scheduling of the processing of the medical data MD.

In some embodiments, the usage data UD can include a queueing time, based on a time from collecting of the one or more pieces of medical data MD to executing of the one or more analyzing services 1521-152N on the one or more pieces of medical data MD. In its simplest implementation, the queueing time can simply be computed as the difference between the latter and the former.

The queueing time is an interesting parameter in that it is indicative of the workload at the data analyzer 1500. In general, the medical data processing system can be configured to reduce the queueing time.

In some embodiments, the usage data UD can further include an analyzing time, based on a time used for executing of the one or more analyzing services 1521-152N on the one or more pieces of medical data MD.

The analyzing time advantageously allows how much computational time is used by the various analyzing services 1521-152N. In general, the medical data processing system can be configured to ensure that analyzing services with a higher analyzing time, and thus generally higher use of computational resources are implemented in those cases where they are used. That is, for instance, if an analyzing service with a higher analyzing time is deemed from the usage data UD not to be often used, the medical data processing system can be configured to reduce the use of the given analyzing service.

In some embodiments, the usage data UD can further include a correlation between use of the one or more pieces of analyzed medical data AMD by the one or more users U1-UN and meta-data associated to the one or more pieces of medical data MD.

This is interesting in that it allows establishing which analyzing services 1520 are perused by the users U1-UN depending on the metadata associated to the medical data MD, so that the most used analyzing services 1520 can be executed with a higher frequency and/or priority on subsequent pieces of medical data MD having similar metadata.

It will be clear that the above examples of usage data UD are not limiting and are intended to show how data related to the usage of the analyzed medical data AMD can be used to efficiently configure the operation of the data analyzer 1500 on the various pieces of medical data MD.

For the data analyzer 1500 to make use of the usage data UD, the medical data processing system 1000 can further include a processing optimizer 1400 configured to control operation of the data analyzer 1500 based on the usage data UD.

In general, the role of the processing optimizer 1400 is to decide amongst the pieces of medical data MD to be processed, and, knowing the amount of available compute resource for various types of analyzing services 1520, which piece(s) of medical data MD should be scheduled to be processed first. Since the compute time is ultimately limited by the maximum amount of compute instances, or indirectly by maximum compute cost per period, this can be treated as an optimization problem where the target is to closest match the minimum time lapse between the acquisition time and the time the user opens the case results for a specific type of analyzing service results.

More specifically, in some embodiments, the processing optimizer 1400 can be configured to control operation of the data analyzer 1500 by controlling which of the one or more analyzing services 1521-152N is executed on which of the one or more pieces of medical data MD.

Alternatively, or in addition, in some embodiments, the processing optimizer 1400 can be configured to control operation of the data analyzer 1500 by controlling a level of computing resources made available for the execution of the one or more analyzing services 1521-152N on the one or more pieces of medical data MD.

Further, alternatively, or in addition, in some embodiments, the processing optimizer 1400 can be configured to control operation of the data analyzer 1500 by controlling a scheduling for executing the one or more analyzing services 1521-152N on the one or more pieces of medical data MD.

Optionally, in some embodiments, site specific constraints can be applied to the processing optimizer 1400 for specific analyzing services 1520. For example, for an analyzing service aimed to support a specific type of disease diagnostics, the processing optimizer 1400 could know that the disease specialist user is only available on some days, for instance due to working hours or shifts, and take this into account when scheduling the processing of the various pieces of medical data MD.

In this respect, in some embodiments, the medical data processing system 1000 can further include a configuration storage 1800, configured to store configuration data CD, related to processing preferences, wherein the processing optimizer 1400 is further configured to control operation of the data analyzer 1500 based on the configuration data CD.

The configuration data can include any predetermined configuration inputted by a manager of the data processing system 1000, so as to constrain the optimization space of the processing optimizer. Information such as the working schedule of the various users U1-UN, their costs per hour, the limit of overtime legally available to each of them, and their experience in different medical fields, could be stored, for instance, relating to the users U1-UN. Alternatively, or in addition, the processing preferences might indicate preferences, or weights, for execution of one or more given analyzing service, for instance because those are believed to be more effective, or because a contract with their provider makes them particularly cost-effective compared to other services, etc.

In some embodiments, the processing optimizer 1400 can include a neural network, where the feedback provided by the usage data UD advantageously allows the system to evolve so at to account for variable preferences of the users. Similarly, the configuration data allows hospital managers to influence the operation of the processing optimizer in accordance with potentially variable constraints and operating conditions.

Preferably, the neural network can be trained based on the usage data UD. Even more preferably, the neural network can be trained through reinforcement learning. In this case, the processing optimizer 1400 can act as an agent, taking decisions on which analyzing services 1520 are executed on which pieces of medical data, and in which order. The type and order of the pieces of analyzed medical data thus follows from how the processing optimizer 1400 is trained. To provide a feedback on the operation of the processing optimizer 1400, an interpreter receiving as input at least the usage data can be implemented as a part the processing optimizer itself, and/or as a part the results manager 1600.

Various usage data UD can be considered to provide a feedback to the operation of the processing optimizer 1400. It will be clear, for instance, the processing optimizer 1400 can be configured to reduce the queueing time, and/or to reduce computation time associated to analyzing services which are less used, etc. In general, by providing the usage data UD as input to the processing optimizer 1400, together with one or more goals defined based on at least the usage data UD, the processing optimizer can be trained to operate the analyzing services 1520 in a manner dependent on said goals, so as to maximize a cumulative reward.

The use of a reinforcement learning in this case is particularly advantageous, as it allows the operation of the processing optimizer 1400 to be trained without providing labelled input/output. In particular, it is difficult to know a-priori which configuration of the analyzing services 1520 can yield the best results for the users U1-UN. By using a reinforcement learning based on the usage data UD, the processing optimizer 1400 can autonomously identify how the various configurations of the analyzing services 1520 leads to an improved usage by the users U1-UN.

In some embodiments, the neural network can be further configured to be continuously trained based on at least the usage data UD. Here, continuously trained can be understood to mean that training of the neural network is executed with some regularity also during the operation, and not only in a single, initial, training phase. In some embodiments, it might be therefore preferable to implement the continuous training in an uninterrupted manner. Alternatively, or in addition, in some embodiments it might be preferable to implement the continuous training in an interrupted but regular manner, for instance by performing the training in a regular manner based on a time interval, for instance on an hourly, daily, and/or weekly basis, preferably based on the usage data US collected during the last time interval prior to the training.

The implementation of a continuous training advantageously allows the processing optimizer 1400 to improve the management of the analyzing services 1520 over time. Moreover, this advantageously allows changes to be reflected in the operation of the processing optimizer. For instance, if one or more of the users U1-UN changes, or if the users change the manner in which they peruse the data, the continuous training advantageously allows the processing optimizer 1400 to take into account those changes and continuously train itself to allow the management of the analyzing services 1520 to reflect those changes.

In some embodiments, as previously indicated, in addition to the usage data, the processing optimizer 1400 can receive as input the configuration data CD. In particular in the case of implementing a neural network in the processing optimizer 1400, the configuration data CD can define the parameters used in the computation of the cumulative reward by the neural network. Alternatively, or in addition, the configuration data CD can define the goals used for the computation of the cumulative reward by the neural network In some embodiments, the processing optimizer 1400 can further receive as input the clinical case associated with the pieces of medical data MD. This allows the processing optimizer 1400 to also consider the clinical case in determining the configuration of the analyzing services 1520 for a given piece of medical data MD. For instance, while two pieces of medical data MD might both relate to chest X-rays, one could be associated to a clinical case involving a heart failure while the other might be associated to a less urgent pathology. This information might be used by the processing optimizer 1400 in determining the configuration of the analyzing services 1500. The clinical case information might then be used as an additional input for computing the cumulative reward. In this manner it is possible to advantageously prioritize the analysis of more urgent pathologies.

The approach described above therefore allows the medical data processing system to make an efficient use of the computational resources used by the data analyzer 1500 based on a feedback obtained in form of the usage data UD and, where applicable, based on a set of preferences, or optimization constraints, provided in form of the configuration data CD.

In addition and in a synergistic combination with this approach, in some embodiments the medical data processing system 1000 can further include a workflow analytics engine 1900, configured to evaluate the usage data UD so as to identify, for a given user U1 of the one or more users U1-UN, how the one or more pieces of analyzed medical data AMD are used by the given user U1.

That is, even assuming that all users U1-UN for a given type of medical data MD prefer the execution of the same analyzing services 1520, it might be that the configuration with which the users U1-UN peruse the output of those services differ. In other words, the workflows of two users might differ, even in the case of similar pieces of medical data MD to be analyzed and even in the case of the same analyzing services being executed on those pieces of medical data. For instance, the order of presentation of the output of those analyzing services 1520 might be different among various users U1-UN due to personal preferences. As another example, the configuration of the analyzed medical data AMD, where allowed by the analyzing services 1521-152N, might also be different for various users, etc.

In order to optimize to the user specific workflows, the system 1000 can also go through an initial learning phase for the workflow analytics engine 1900, as previously described for the processing optimizer 1400. That is, initially the processing and presentation of results of the data analyzer 1500 can be simply presented in a first come first serve ranking and displayed the same way to all user U1-UN. Subsequently, through learning based on the usage data, workflows specific to the various users U1-UN can be learned. A reinforcement type of learning can be well suited for this application, but other types of learning approaches can also be implemented.

In general, for a given user U1-UN, the usage data UD related to one or more pieces of analyzed medical data AMD can be considered so as to rank, for a given user, each case, the output of the analyzing services 1520 which the user usually peruses, and the time that the user typically reads them. In this manner, in an initial learning phase, results from the analyzing services 1520 can be presented in the first come first serve order to all users. When a given user decides to do any of opening, using, annotating, or accepting the analyzing service results for a given case, these actions can be assigned as a reward for the workflow analytics engine's reinforcement learning.

In particular, in some embodiments, any of the following information can be gathered as usage data UD for the purpose of providing an input to the workflow analytic engine:

the user and/or user profile that used a given analyzing service, as that may indicate disease diagnostic specialty of the particular user or user preference, timestamp, and the elapsed time between acquisition and the time of analyzing service use, as this is an indication of the reading turnaround time requirement, correction and/or confirmation of the results from the analyzing service, which is considered a stronger reward than simply opening to view the results, and conversely, the absence of use of the results will be considered as a negative feedback to the agent to provide similar types of results to this user next time.

In general, the workflow analytics engine 1900 can be trained based on the usage data UD to act as an agent to attempt to maximize the use of the results overall, by optimizing the presentation and/or configuration of the types of analyzing service results to the most likely user at the appropriate time. That is, the results most likely to be used by a particular user at a particular time can be recommended by the medical data processing system 1000 in the most accessible and attractive user interface layout, for the given user.

As can be gathered from the above, to account for the different workflows, the results manager 1600 can further be configured to output the one or more pieces of analyzed medical data AMD to a plurality of output devices 1701-170N based on the results of the evaluation of the workflow analytics engine 1900. In some embodiments, the decision on how and to output the one or more pieces of analyzed medical data AMD to a given output device 1701-170N can be associated to the user U1-UN currently operating the given output device 1701-170N.

In some embodiments, the workflow analytics engine 1900 can include a neural network, where the feedback provided by at least the usage data UD advantageously allows the system to evolve so at to keep into account variable preferences of the users.

Preferably, the neural network can be trained based on the usage data UD. Even more preferably, the neural network can be trained through reinforcement learning. In this case, the workflow analytics engine 1900 can act as an agent, taking decisions on how the results of the analyzing services 1520 are shown to one or more users U1-UN. The visualization configuration and/or order of the pieces of analyzed medical data AMD can thus depend on how the workflow analytics engine 1900 is trained.

To provide a feedback on the operation of the workflow analytics engine 1900, an interpreter receiving as input at least the usage data UD can be implemented as a part the workflow analytics engine itself, and/or as a part the results manager 1600.

Various usage data UD can be considered to provide a feedback to the operation of the workflow analytics engine 1900. It will be clear, for instance, the workflow analytics engine 1900 can be configured to visualize the pieces of analyzed medical data in an order and/or with a configuration which is preferred by each given user U1-UN, which might differ from user to user. For instance, a user U1 might prefer to be shown first the results from an analyzing service 1521, while a user U2 might prefer to be shown first the results from a different analyzing service 1522. Alternatively, or in addition, the order and/or configuration might also be dependent on the type of medical data MD which is being analyzed. For instance, the same user U1 might prefer a given configuration when visualizing analyzed medical data AMD for a chest X-ray and a different configuration when visualizing analyzed medical data AMD for a leg X-ray.

In general, the usage data UD can thus be provided as input to the workflow analytics engine 1900, together with one or more goals based on at least the usage data UD. The workflow analytics engine 1900 can then be trained to configure the visualization of the pieces of analyzed medical data AMD in a manner dependent on said goals, so as to maximize a cumulative reward. In some embodiments, the cumulative reward can be computed independently for one or more single user U1-UN to train the workflow analytics engine 1900 independently for each such user.

The use of a reinforcement learning in this case is particularly advantageous, as it allows the operation of the workflow analytics engine 1900 to be trained without providing labelled input/output. In particular, it is difficult to known a-priori which visualization of the pieces of analyzed medical data AMD can yield the best results for any given user U1-UN, as this involves a high level of personal preferences. By using a reinforcement learning based on the usage data UD, the workflow analytics engine 1900 can autonomously identify how the various visualizations lead to an improved feedback by the users U1-UN.

In some embodiments, if the visualization configuration and/or order resulting from the workflow analytics engine 1900 is changed by the user, this can be considered as a negative feedback. If, on the other hand, the configuration and/or order of the pieces of analyzed medical data AMD is not changed, this can be considered as a positive feedback. In such simple implementation, the cumulative reward can thus be computed as a sum of the positive and negative feedbacks.

In some embodiments, the cumulative reward can include more complicated goals formulations. For instance, a change of configuration visualization of the pieces of analyzed medical data AMD can have a different weight than a change of visualization order of the pieces of analyzed medical data AMD, so that different weights can be assigned to the two events, in the computation of the cumulative reward.

In some embodiments, the neural network can be further configured to be continuously trained based on at least the usage data UD. Continuously trained can be understood as previously described.

The implementation of a continuous training advantageously allows the workflow analytics engine 1900 to improve the output of the pieces of analyzed medical data AMD over time. Moreover, this advantageously allows changes to be reflected in the operation of the workflow analytics engine 1900. For instance, if one or more of the users changes the manner in which they peruse the data, the continuous training advantageously allows the workflow analytics engine 1900 to take into account those changes and continuously train itself to allow the output configuration of the pieces of analyzed medical data AMD to reflect the changes.

In some embodiments, the neural network for the workflow analytics engine 1900 can use training results associated to one or more users in consideration when training for another user. That is, the neural network can have a plurality of profiles, associated to the users U1-UN, as the perusal of the data might be user dependent. The neural network can then use the trained configuration associated to one or more profiles in consideration when training another profile. This is advantageous, for instance, when a new user profile is trained, so that instead of starting from scratch, the training results from other users can be used, as those are likely to provide a better start for the training.

In some embodiments, the workflow analytics engine 1900 can further receive as input the clinical case associated to the pieces of analyzed medical data AMD and/or associated to the pieces of medical data MD. This allows the workflow analytics engine 1900 to also consider the clinical case in determining the output configuration for a given piece of analyzed medical data AMD. For instance, while two pieces of analyzed medical data AMD might both relate to chest X-rays, one could be associated with a clinical case involving a heart failure while the other might be associated to a clinical case involving a pneumonia. This information might be used by the workflow analytics engine 1900 in determining the output configuration of the pieces of analyzed medical data AMD.

The analyzer 1500, manager 1600, optimizer 1400, and engine 1900 may be implemented by a same processor or different processors. These components are or are provided as one or more processor executing instructions.

Figure 2:
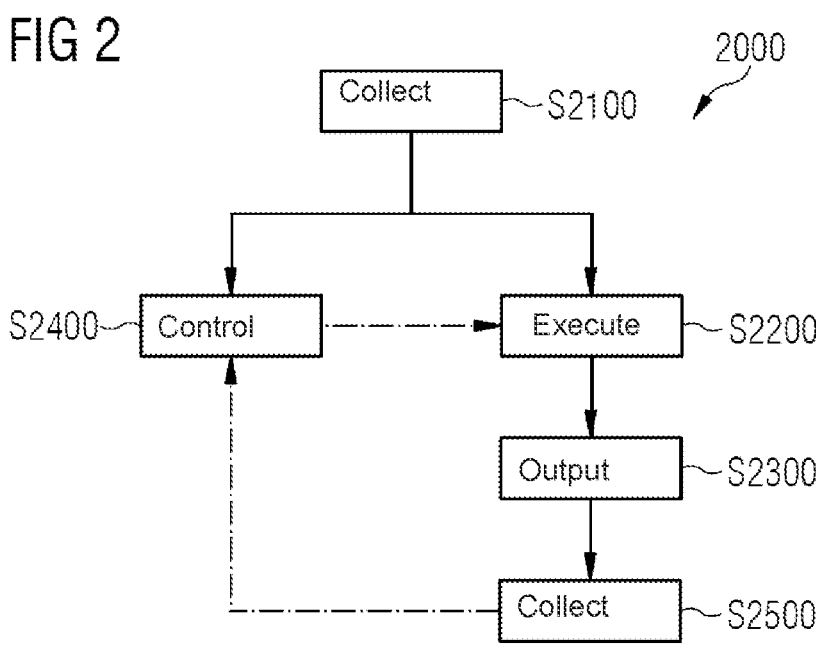
FIGS. 2-4 schematically illustrates possible operations of the medical data processing system 1000, according to various embodiments.

FIG. 2 schematically illustrates a medical data processing method 2000.

As can be seen, the method 2000 can include an act S2100 of collecting one or more first pieces of medical data MD from one or more input devices 1101-110N, an act S2200 of executing one or more analyzing services 1521-152N on the one or more pieces of medical data MD, and an act S2300 of outputting one or more corresponding pieces of analyzed medical data AMD. The method 2000 can further include an act S2500 of collecting S2500 usage data UD related to how the one or more analyzing services 1521-152N are executed at the executing act S2200 and/or how the one or more pieces of analyzed medical data AMD are used by one or more users U1-UN. Those acts can thus implement a training phase of the method 2000.

In a controlling act S2400, based on such training on previous data, as schematically illustrated by the dotted line, the executing act S2200 for one or more second pieces of medical data MD, subsequent to the one or more first pieces of medical data MD, can be controlled based on the usage data UD. In this manner, it is advantageously possible to improve the efficiency of the use of the analyzing services, as previously described.

That is, the method 2000 allows a continuous training of the controlling act S2400 based on the previously generated usage data, so that changes into users U1-UN, policies, user's perusal of the pieces of analyzed medical data AMD, etc. can be tracked by the method 2000. In other words, the training can be performed in parallel to the controlling of the execution of the analyzing services 1521-152N.

An embodiment can thus relate to a method for training a neural network included in a processing optimizer 1400. As previously described, the processing optimizer 1400 can be configured to control operation of one or more analyzing services 1521-152N of a data analyzer 1500 in a medical data processing system 1000. The data analyzer 1500 can be configured for converting one or more pieces of medical data AMD into one or more pieces of analyzed medical data AMD. The method for training can include an act S2500 of collecting usage data UD, wherein the usage data UD relate to how the one or more analyzing services 1521-152N are executed and/or how the one or more pieces of analyzed medical data AMD are used by one or more users U1-UN. The method for training can further include an act of training the neural network through reinforcement learning on the basis of at least the usage data UD.

The above-described training method can thus be used for training a neural network which can carry out at least the controlling act S2400.

It will be clear that, for the purpose of training, in some embodiments, the neural network can also use as input the neural network configuration which resulted in the usage data UD. That is, for training at a given time X, at which the usage data UD is received by the neural network, the neural network configuration at a time Y prior to X can also be used as a basis for the training. In particular, it is preferable that the neural network configuration at the time Y is the one which resulted in the usage data UD at time X.

In this manner, the neural network can be advantageously trained through reinforcement learning in a continuous manner. In some embodiments, this might result in an initial operating phase in which the neural network operates based on a predetermined condition, as no usage data is yet available. In this case, however, considering the rather short time required for obtaining the first usage data UD, a predetermined configuration might be considered to be sufficient for this initial operating phase. In an exemplary implementation, the predetermined configuration might be a first-come-first-served implementation. In this case, for the processing optimizer 1400, the pieces of medical data MD would be analyzed on a first-come-first-served order. Alternatively, or in addition, for the workflow analytics engine 1900, the pieces of analyzed medical data AMD would be outputted on a first-come-first-served order.

In alternative, or in addition, the neural network can undergo a training based on pieces of medical data MD that have been previously analyzed and the usage data UD of which has been previously collected. That it, the neural network can be trained based on historical data from a medical data processing system including at least a data analyzer 1500 and a results manager 1600. In this manner, it can be advantageously ensured the neural network is adequately trained as soon as in operation.

Figure 3:
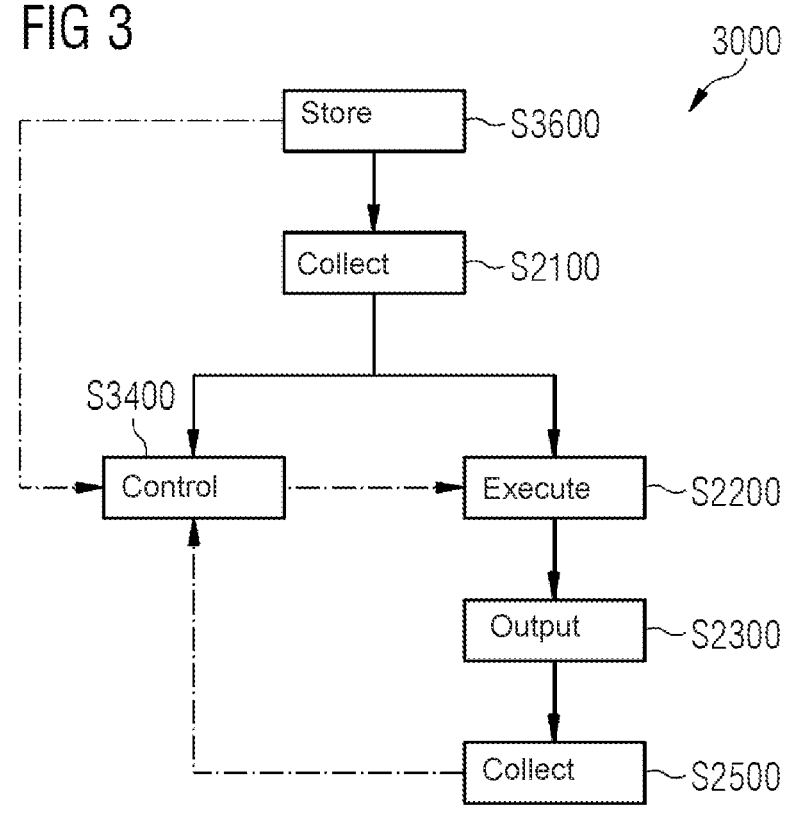

FIG. 3 schematically illustrates a further method 3000, further including an act S3600 of storing configuration data CD, related to processing preferences, as previously described. In this embodiment, as schematically illustrated by the dotted lines, the act S3400 of controlling can further be configured to control the executing act S2200 for the one or more second pieces of medical data MD, based on the configuration data CD as previously described.

Figure 4:
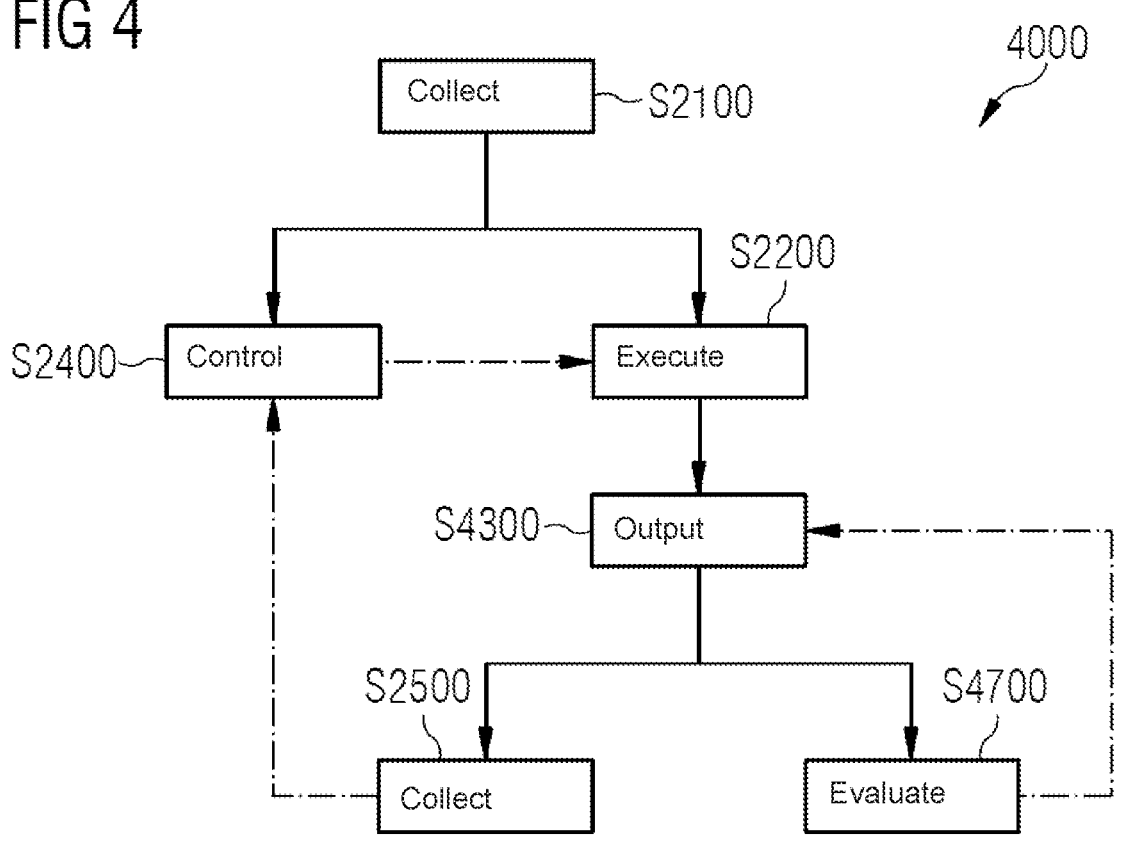

FIG. 4 schematically illustrates a further method 3000, further including an act S4700 of evaluating the usage data UD so as to identify, for a given user U1 of the one or more users U1-UN, how the one or more pieces of analyzed medical data AMD are used by the given user U1. In this embodiment, the outputting act S4300 can thus be further configured to output the one or more pieces of analyzed medical data AMD to a plurality of output devices 1701-170N based on the results of the evaluating act S4700.

A further embodiment can thus relate to a method for training a neural network included in a workflow analytics engine 1900. As previously described, the workflow analytics engine 1900 can be configured to control an output configuration of one or more pieces of medical data AMD in the medical data processing system 1000. That is, the neural network can control the execution of outputting act S4300. The method can include an act S2500 of collecting usage data UD, wherein the usage data UD relate to how the one or more pieces of medical data AMD are visualized by one or more users U1-UN. The method can further include an act of training the neural network through reinforcement learning on the basis of at least the usage data UD.

The above-described training method can thus be used for training a neural network which can carry out at least the controlling act S2400.

The training considerations expressed for the neural network included in the processing optimizer 1400 can also apply to the neural network included in the workflow analytics engine 1900.

While in the embodiments described above it has been indicated that the neural networks can be trained with a reinforcement learning approach, with the advantages discussed, the invention is not limited to this configuration and in some embodiments one or more of the neural networks might be trained with a different approach, for instance supervised learning or unsupervised learning.

In alternative, or in addition, one or more of the neural networks might have a first training phase with a first approach, such as supervised learning, and a second training phase with a different approach, such as a reinforcement learning. This last implementation can be particularly advantageous, for instance, in cases in which the first phase corresponds to an initial training of the neural network, prior to its use in the medical data processing system 1000, while the second phase corresponds to a later training of the neural network, during its use in the medical data processing system 1000.

It thus follows from the description above that the embodiments allows a medical data processing system and/or a medical data processing method to ensure efficient use of the computational resources available for the data analyzer, as well as ensuring ideal configuration of the workflow for each user in perusing the results of the data analyzer. Besides allowing an efficient use of resources, both technical and human, the embodiments therefore increase the quality of the diagnosis that can be derived from the analyzed pieces of medical data, thus also increasing the quality of care for patients.

While some of the above embodiments have been described in terms of method acts, the embodiments can also be implemented as a software. In particular, embodiments can further relate to one or more computer programs including instructions which, when the program is executed by a computer, cause the computer to carry out any of the methods previously described.

Summarizing, above, techniques have been described that help to analyze the medical data in a manner which makes efficient use of the computational resources allocated thereto, while also considering hospital policies and allowing a more efficient use of the analysis by the medical personnel in charge of the diagnosis.

While various embodiments have been described above, each comprising one or more features, it will be clear that the invention is not limited to the described embodiments in those specific forms. The skilled person will recognize that additional embodiments can be implemented by combining one or more feature from any of the embodiments with one or more features from any other embodiment.

The invention claimed is:

1. A medical data processing system comprising:
a medical data storage implemented by a memory coupled with a processor, the medical data storage configured to store one or more pieces of medical data from one or more input devices,
a data analyzer implemented by the processor, the data analyzer configured to execute one or more analyzing services on the one or more pieces of medical data so as to output one or more corresponding pieces of analyzed medical data,
a results manager implemented by the processor, the results manager configured to collect usage data related to how the one or more pieces of analyzed medical data are analyzed by the data analyzer and/or used by one or more users at a particular hospital institution, wherein the usage data comprises at least a queueing time, based on a time from collecting of the one or more pieces of medical data to executing of the one or more analyzing services on the one or more pieces of medical data and an analyzing time based on a time used for executing of the one or more analyzing services on the one or more pieces of medical data, and
a processing optimizer implemented by the processor, the processing optimizer configured to control operation of the data analyzer by prioritizing execution of specific analyzing services of the one or more analyzing services based on the usage data and a level of computing resources made available for the execution of the one or more analyzing services on the one or more pieces of medical data so that an output most likely to be used by a particular user at a particular time at a particular hospital institution is provided by the one or more analyzing services, wherein the processing optimizer comprises a neural network trained through reinforcement learning, wherein the neural network is configured to receive at least the usage data as input for computing a cumulative reward related to the operation of the data analyzer.

2. The medical data processing system according to claim 1, wherein the processing optimizer is further configured to control operation of the data analyzer by control of: which of the one or more analyzing services is executed on which of the one or more pieces of medical data or a level of computing resources made available for the execution of the one or more analyzing services on the one or more pieces of medical data.

3. The medical data processing system according to claim 1, wherein the neural network is configured to be continuously trained based on at least the usage data.

4. The medical data processing system according to claim 1, wherein the neural network is configured to further receive at least configuration data as additional input for computing the cumulative reward.

5. The medical data processing system according to claim 1, wherein the neural network is configured to further receive clinical case information associated to the one or more pieces of medical data as additional input for computing the cumulative reward.

6. The medical data processing system according to claim 1, wherein the usage data further comprises:

correlation between use of the one or more pieces of analyzed medical data by the one or more users and meta-data associated to the one or more pieces of medical data.

7. The medical data processing system according to claim 1, further comprising a configuration storage implemented by the memory coupled with the processor, the configuration storage configured to store configuration data, related to processing preferences, wherein the processing optimizer is further configured to control operation of the data analyzer based on the configuration data.

8. The medical data processing system according to claim 1, further comprising a workflow analytics engine implemented by the processor, the workflow analytics engine is configured to evaluate the usage data so as to identify, for a given user of the one or more users, how the one or more pieces of analyzed medical data are used by the given user, wherein the results manager is further configured to output the one or more pieces of analyzed medical data to a plurality of output devices based on the results of the evaluation of the workflow analytics engine.

9. The medical data processing system according to claim 8, wherein the workflow analytics engine comprises a second neural network trained through reinforcement learning, wherein the second neural network is configured to receive at least the usage data as input for computing a cumulative reward related to the output of the one or more pieces of analyzed medical data to the plurality of output devices.

10. The medical data processing system according to claim 9, wherein the second neural network is configured to be continuously trained based on at least the usage data.

11. The medical data processing system according to claim 9, wherein the second neural network is configured to further receive clinical case information associated to the one or more pieces of analyzed medical data and/or associated to the one or more pieces of medical data as additional input for computing the cumulative reward.

* * * * *